US007634310B2

(12) United States Patent
Lee et al.

(10) Patent No.: US 7,634,310 B2
(45) Date of Patent: Dec. 15, 2009

(54) METHOD AND APPARATUS FOR ATRIAL FIBRILLATION DETECTION BASED ON VENTRICULAR CYCLE LENGTHS

(75) Inventors: Brian B. Lee, Golden Valley, MN (US); Eric J. Panken, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 38 days.

(21) Appl. No.: 11/554,275

(22) Filed: Oct. 30, 2006

(65) Prior Publication Data

US 2008/0188764 A1 Aug. 7, 2008

(51) Int. Cl.
*A61B 5/024* (2006.01)

(52) U.S. Cl. .................... 600/515; 600/509; 600/523

(58) Field of Classification Search ............ 324/76.12; 600/515, 516, 518, 521, 523; 607/5, 9, 11, 607/14, 19, 27
See application file for complete search history.

(56) References Cited

U.S. PATENT DOCUMENTS

| | | | | |
|---|---|---|---|---|
| 5,086,772 A | * | 2/1992 | Larnard et al. | 607/4 |
| 5,117,824 A | | 6/1992 | Keimel et al. | |
| 5,319,569 A | * | 6/1994 | Nichols et al. | 702/199 |
| 5,509,925 A | * | 4/1996 | Adams et al. | 607/5 |
| 5,591,215 A | | 1/1997 | Greenhut et al. | |
| 5,968,079 A | * | 10/1999 | Warman et al. | 607/5 |
| 6,091,988 A | * | 7/2000 | Warman et al. | 607/5 |
| 6,490,479 B2 | | 12/2002 | Bock | |
| 6,961,616 B2 | * | 11/2005 | Kramer et al. | 607/25 |
| 7,031,765 B2 | * | 4/2006 | Ritscher et al. | 600/518 |
| 7,082,328 B2 | * | 7/2006 | Funke | 607/9 |
| 7,099,716 B1 | * | 8/2006 | Levine | 607/28 |
| 7,120,485 B2 | * | 10/2006 | Glass et al. | 600/515 |
| 2002/0065473 A1 | | 5/2002 | Wang et al. | |
| 2002/0128564 A1 | * | 9/2002 | Carlson et al. | 600/509 |
| 2004/0092836 A1 | * | 5/2004 | Ritscher et al. | 600/518 |
| 2005/0004486 A1 | | 1/2005 | Glass et al. | |
| 2007/0270704 A1 | * | 11/2007 | Ghanem et al. | 600/521 |

OTHER PUBLICATIONS

Cohen, Richard et al., "A quantitative model for the ventricular response during atrial fibrillation," IEEE Trans Biomed Eng. Dec. 1983; 30(12):769-81, USA.
International Search Report for PCT/US2007/081600.

* cited by examiner

*Primary Examiner*—Carl H Layno
*Assistant Examiner*—Luther G Behringer
(74) *Attorney, Agent, or Firm*—Michael C. Soldner (57) ABSTRACT

A method and apparatus for detecting atrial arrhythmias include acquiring a cardiac signal comprising R-waves. Differences between pairs of consecutive R-R intervals occurring during a first time interval are computed from the cardiac signal. An atrial arrhythmia is detected subsequent to the first time interval in response to the computed differences. Storage of the cardiac signal is triggered in response to the atrial arrhythmia detection.

28 Claims, 10 Drawing Sheets

METHOD AND APPARATUS FOR ATRIAL FIBRILLATION DETECTION BASED ON VENTRICULAR CYCLE LENGTHS

REFERENCE TO RELATED APPLICATIONS

Cross-reference is hereby made to commonly assigned related U.S. application Ser. No. 11/321,183, entitled "METHOD AND APPARATUS FOR DETECTION OF TACHYARRHYTHMIA USING CYCLE LENGTHS", incorporated herein by reference in its entirety.

TECHNICAL FIELD

The invention relates generally to implantable medical devices and, in particular, to a device and method for using irregularity of ventricular cycle lengths for detecting atrial arrhythmias.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The resulting ventricular cycle lengths will be irregular and will depend on the different states of refractoriness of the AV-node.

In the past, atrial arrhythmias have been largely undertreated due to the perception that these arrhythmias are relatively benign. As more serious consequences of persistent AT/AF have come to be understood, such as an associated risk of relatively more serious ventricular arrhythmias and stroke, there is a greater interest in monitoring and treating atrial arrhythmias than in the past. In single chamber implantable devices or in subcutaneously implanted or external monitoring devices, an atrial EGM signal is not always available for use in detecting and discriminating atrial arrhythmias. Detection and discrimination of atrial arrhythmias is important, however, in properly diagnosing and treating a patient and preventing more serious, life-threatening or debilitating events.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
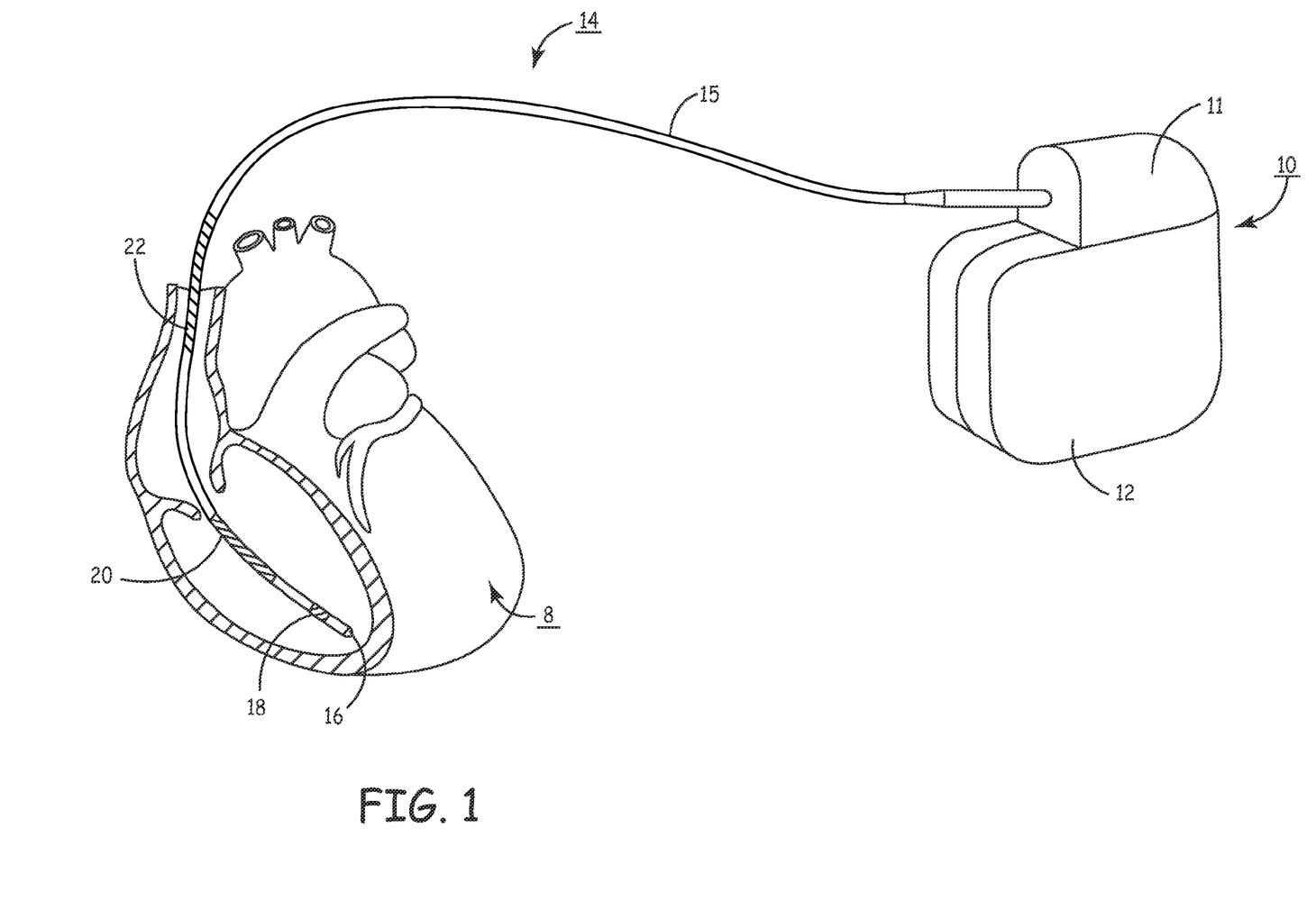
FIG. 1 depicts an implantable medical device (IMD) in which methods described herein for detecting atrial arrhythmias may be implemented.

FIG. 1 depicts an implantable medical device 10 embodied as an implantable cardiovertor defibrillator (ICD), in which methods described herein for detecting atrial arrhythmias may be implemented. Various embodiments of the invention may be implemented in numerous types of implantable or external medical devices which are capable of sensing cardiac signals and include pacemakers, ECG monitors, and hemodynamic monitors. IMD 10 is provided for sensing intrinsic heart activity and delivering cardiac stimulation pulses in the form of pacing, cardioversion or defibrillation therapy, as appropriate, in the right ventricle.

IMD 10 includes a hermetically sealed housing 12 enclosing internal IMD circuitry (not shown in FIG. 1) and a connector block 11 for receiving lead 14 and electrically coupling lead 14 to circuitry enclosed in housing 12. IMD 10 is shown in communication with a patient's heart 8 by way of a transvenous lead 14. Lead 14 includes an insulated lead body 15 carrying elongated conductors extending to each of a tip electrode 16, ring electrode 18, right ventricular (RV) coil electrode 20 and superior vena cava (SVC) coil electrode 22. A remote indifferent can electrode may be formed as part of the outer surface of the IMD housing 12. The tip and ring electrodes 16 and 18 and the remote indifferent can electrode can be selectively employed to provide unipolar or bipolar pace/sense electrode combinations for pacing and sensing functions. The high voltage coil electrodes 20 and 22 are used for delivering high voltage cardioversion and defibrillation shock pulses to heart 8 in response to detecting tachycardia or fibrillation. In some embodiments, coil electrodes 20 and 22 may be used in combination with a can electrode incorporated in IMD housing 10 for delivering high voltage shock pulses.

While one particular embodiment of an IMD is shown in FIG. 1, it is recognized that alternative embodiments may include other lead and electrode configurations. For example, IMD 10 may be coupled to a coronary sinus lead advanced into a cardiac vein via the coronary sinus for sensing and stimulating in the left heart chambers. In addition to the lead-mounted electrodes, IMD 10 may include one or more subcutaneous cardiac sensing electrodes formed as uninsulated portions of the IMD housing 12 or included in the connector block 11.

It is understood that IMD 10 may be adapted to operate as a single chamber device, dual chamber device or multi-chamber device. Furthermore, it is recognized that embodiments of the present invention may be practiced in a single chamber, dual chamber or multi-chamber implantable cardiac pacemaker that does not include cardioversion and defibrillation functions, or in cardiac monitoring devices that do not include therapy delivery functions.

While the particular IMD system with associated leads and electrodes illustrated in FIG. 1 relies on intracardiac electrodes, numerous implantable cardiac monitoring, pacemaker or other IMD system configurations are possible, which may include one or more leads deployed in transvenous, subcutaneous, or epicardial locations. The lead and electrode arrangements will depend on the particular application. Embodiments of the invention may also include subcutaneous cardiac monitoring, pacemaker or ICD systems in which electrodes are formed as a part of the device housing and/or carried by subcutaneous leads for sensing and/or stimulating the heart without the use of intracardiac electrodes. For example, embodiments of the invention may be implemented in an subcutaneously implantable loop recorder used for monitoring ECG signals, such as the Reveal® Implantable Loop Recorder available from Medtronic, Inc., Minneapolis, Minn. Alternative embodiments may include external devices relying on skin surface electrodes for acquiring cardiac signals.

Figure 2:
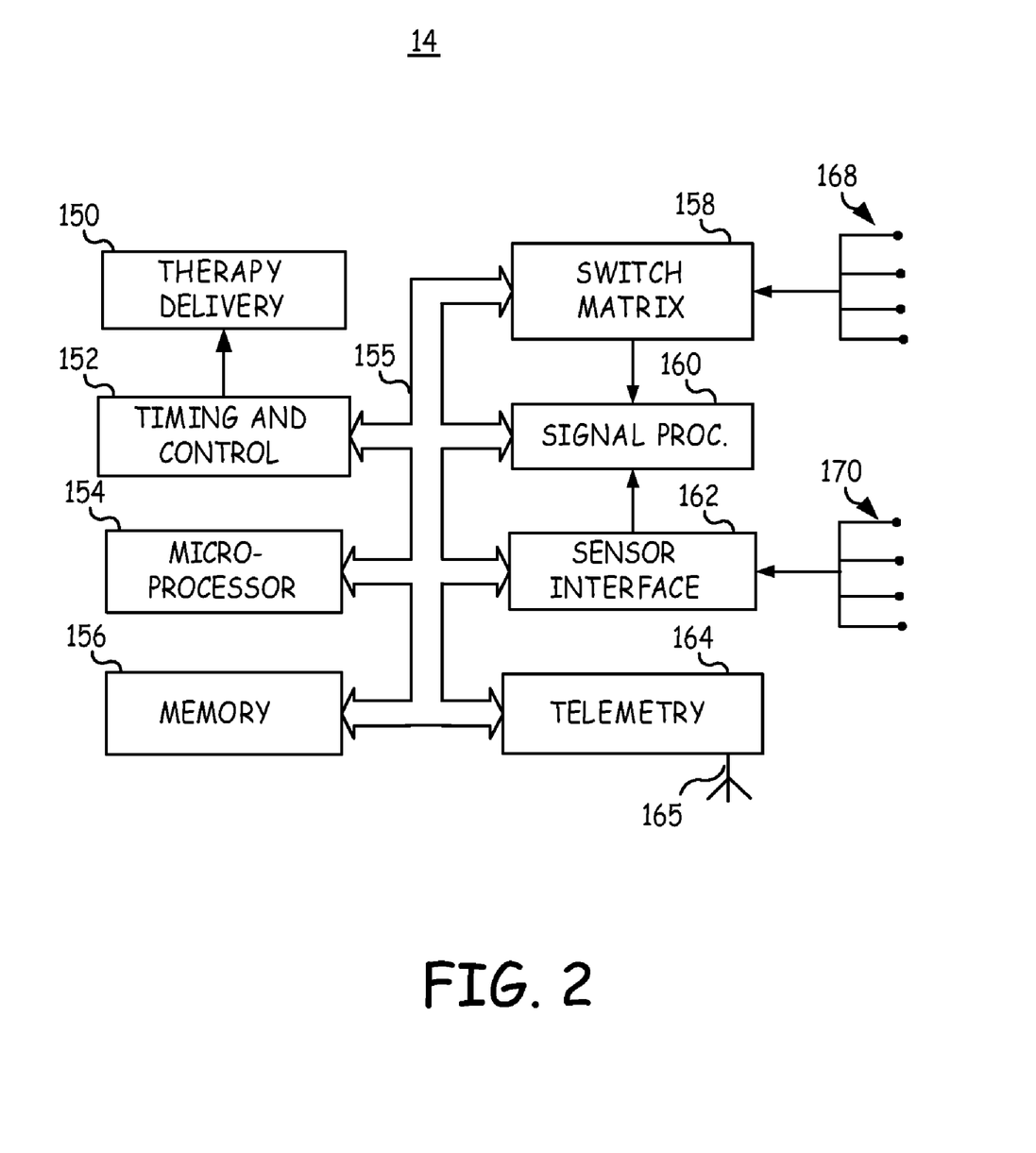
FIG. 2 is a functional block diagram showing some of the components typically included in an implantable cardiac stimulation device such as the IMD shown in FIG. 1.

FIG. 2 is a functional block diagram showing some of the components typically included in an implantable cardiac stimulation device such as the IMD 10 shown in FIG. 1. IMD 10 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 10 via a data/address bus 155. IMD 10 includes therapy delivery module 150 for delivering electrical stimulation therapies, such as cardiac pacing therapies and arrhythmia therapies including cardioversion/defibrillation shocks, under the control of timing and control 152. Therapy delivery module 150 is typically coupled to two or more electrode terminals 168 via a switch matrix 158. Switch matrix 158 is used for selecting which electrodes and corresponding polarities are used for delivering electrical stimulation pulses.

Cardiac electrical signals are sensed for diagnosing a cardiac rhythm and determining when an electrical stimulation therapy is needed and in controlling a stimulation mode and the timing of stimulation pulses. Electrodes used for sensing and electrodes used for stimulation may be selected via switch matrix 158. When used for sensing, electrode terminals 168 are coupled to signal processing circuitry 160 via switch matrix 158. Signal processor 160 includes sense amplifiers and may include other signal conditioning circuitry and an analog to digital converter. Electrical signals may then be used by microprocessor 154 for detecting physiological events, such as detecting and discriminating cardiac arrhythmias. Signal processing circuitry 160 may include event detection circuitry generally corresponding to R-wave detection circuitry as disclosed in U.S. Pat. No. 5,117,824 (Keimel, et al.), hereby incorporated herein by reference in its entirety. R-waves detected by signal processing circuitry 160 are used by microprocessor 154 for computing RR intervals and RR interval differences for use in detecting atrial arrhythmias based on RRI irregularities.

Arrhythmia detection algorithms may also be implemented for detecting ventricular tachycardia (VT), ventricular fibrillation (VF). RR intervals are commonly used for detecting ventricular arrhythmias. Additional information obtained such as R-wave morphology, slew rate, other event intervals (P-R intervals) or other sensor signal information may be used in detecting, confirming or discriminating an arrhythmia. Reference is made to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals, all of which patents are incorporated herein by reference in their entirety.

In response to an arrhythmia detection, a programmed arrhythmia therapy is delivered by therapy delivery module 150 under the control of timing and control 152. A description of high-voltage output circuitry and control of high-voltage shock pulse delivery is provided in the above-incorporated '186 Olson patent. Typically, a tiered menu of arrhythmia therapies are programmed into the device ahead of time by the physician and stored in memory 156, which can include anti-tachycardia pacing, cardioversion shocks, and defibrillation shocks of varying intensities.

IMD 10 may additionally be coupled to one or more physiological sensors via physiological sensor terminals 170. Physiological sensors may include pressure sensors, accelerometers, flow sensors, blood chemistry sensors, activity sensors or other physiological sensors known for use with implantable cardiac stimulation devices. Physiological sensors may be carried by leads extending from IMD 10 or incorporated in or on the IMD housing.

The operating system includes associated memory 156 for storing a variety of programmed-in operating mode and parameter values that are used by microprocessor 154. The memory 156 may also be used for storing data compiled from sensed EGM and physiological signals and/or relating to device operating history for telemetry out on receipt of a retrieval or interrogation instruction.

IMD 10 further includes telemetry circuitry 164 and antenna 165. Programming commands or data are transmitted during uplink or downlink telemetry between telemetry circuitry 164 and external telemetry circuitry included in a programmer or monitoring unit.

Figure 3:
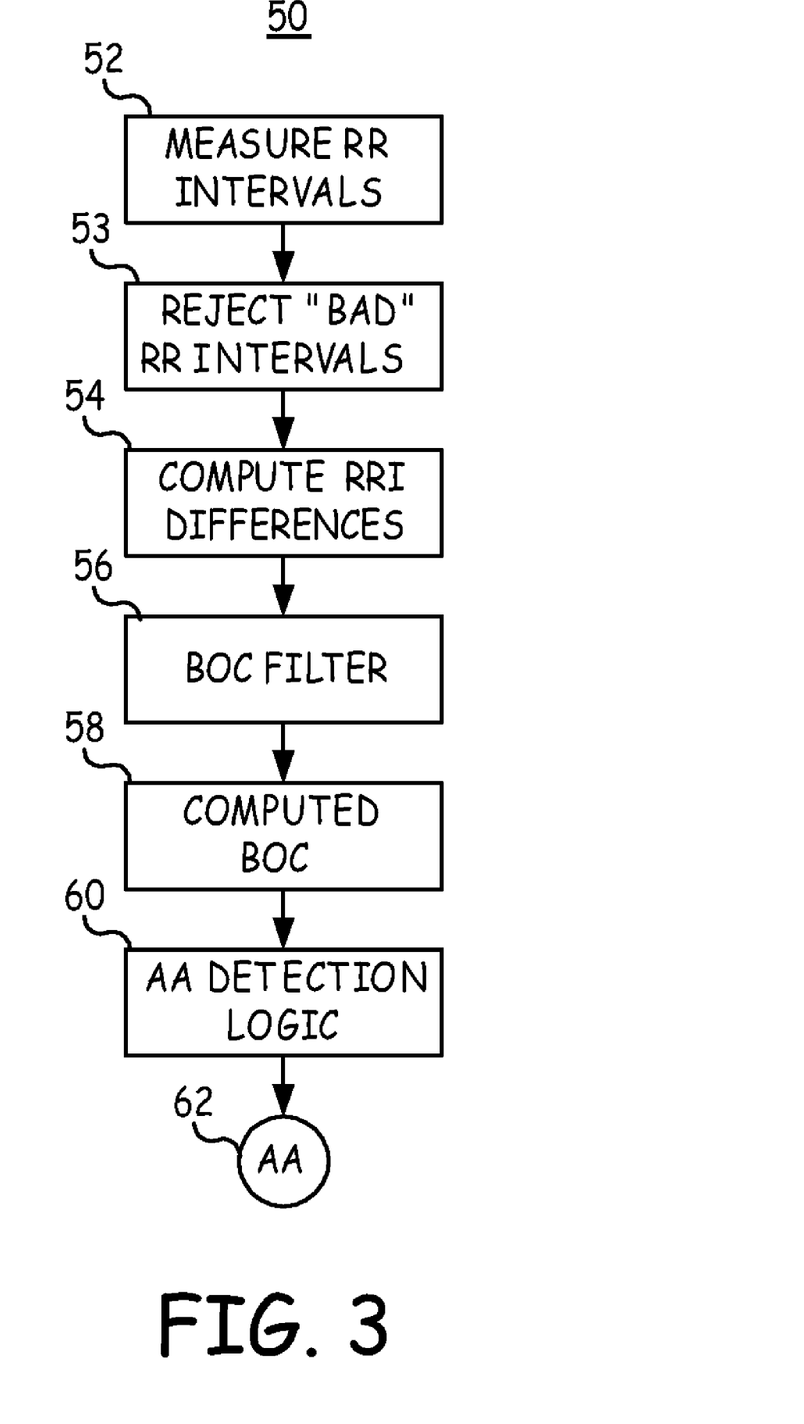
FIG. 3 is a block diagram providing an overview of a method for detecting an atrial arrhythmia using R-R interval measurements.

FIG. 3 is a block diagram providing an overview of a method for detecting an atrial arrhythmia using R-R interval measurements. The block diagram of method 50, as well as other flow charts and functional block diagrams shown herein, are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 50 may be operating continuously as long as sensed R events are available for computing RR intervals. Alternatively, method 50 may be initiated in response to detecting a high ventricular rate or detection of a potential ventricular arrhythmia. At block 52, RR intervals are measured between consecutive R-waves sensed by the IMD. RR intervals may be rejected at block 53 according to noise rejection algorithms or according to EGM signal quality or RR interval acceptance criteria. At block 54, the difference between each consecutive pair of accepted RR intervals is computed ($\delta RRI_n$). The $\delta RRI$ data computed at block 54 is provided to a bin occupancy count (BOC) filter at block 56. BOC filter 56 receives the stream of $\delta RRI$ data and updates a bin counter as needed in response to each $\delta RRI$ value. A number of bins are defined for multiple $\delta RRI$ ranges. BOC filter 56 computes a count of occupied bins, bin occupancy count (BOC) 58, which is provided to a detection logic block 60. Atrial arrhythmia (AA) detection logic block 60 detects an atrial arrhythmia as indicated at 62 based on the BOC. The number of occupied bins is a measure of the RR interval irregularity, providing evidence of an atrial arrhythmia.

Figure 4:
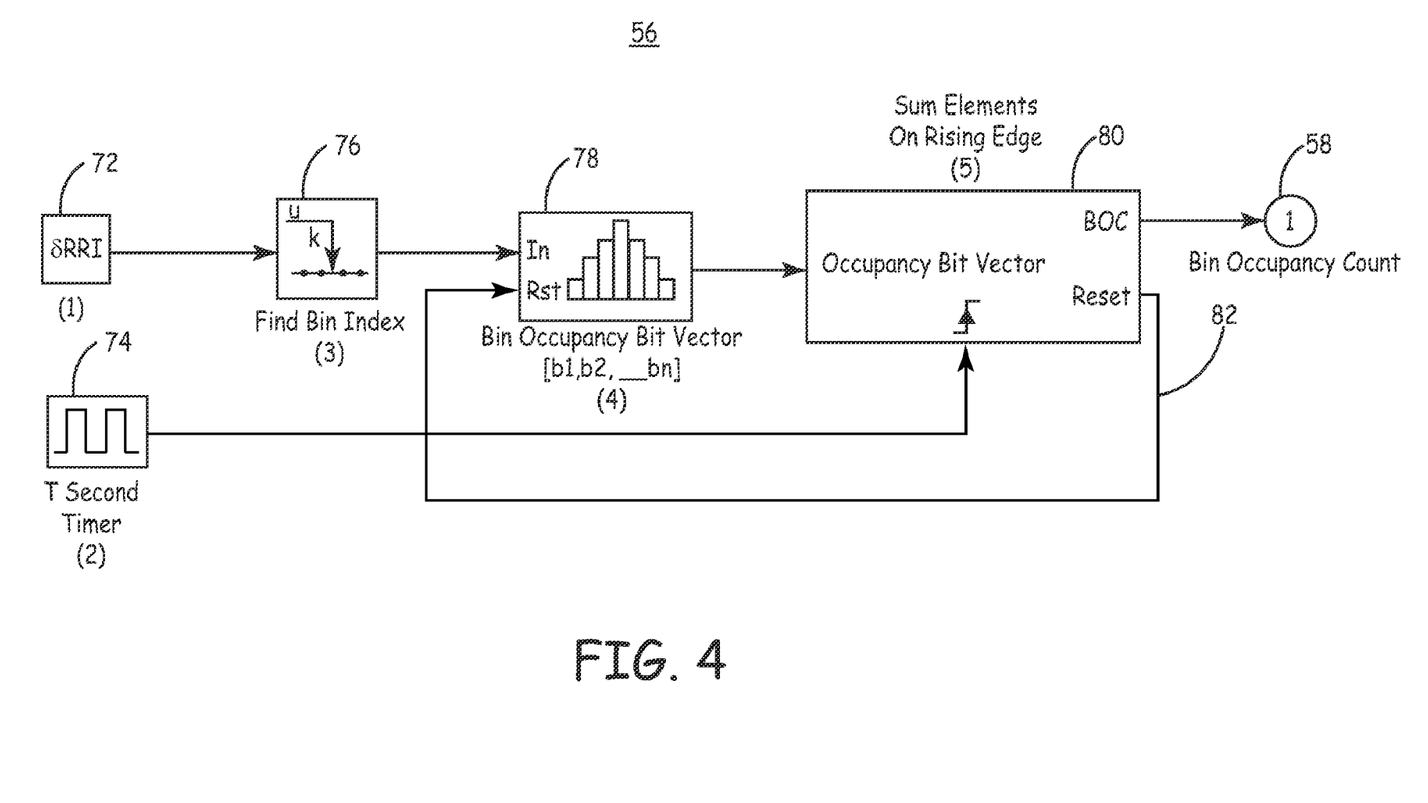
FIG. 4 is a functional block diagram of the bin occupancy count filter shown in FIG. 3.

FIG. 4 is a functional block diagram of the BOC filter 56 shown in FIG. 3. Input block 72 provides a stream of $\delta RRI$ data. At block 76, a bin index (k) is determined for a given $\delta RRI$. Determining the bin index may be performed using binary search, linear search or other appropriate search methods for determining the bin corresponding to the $\delta RRI$ range in which the input $\delta RRI$ value falls. For equally spaced bin edges, $A_O, \ldots A_N$, direct address calculation may be performed to compute the bin index as:

$$k_n = \{(\delta RRI_n - A_O)/\text{bin width}\} + 1.$$

Block 78 is a bin occupancy bit vector (b1, b2, b3, etc.) which stores a bit value for each bin. The bin value indicates whether the bin is occupied, i.e., whether a bin index corresponding to a given bin has been determined for at least one $\delta RRI$ received as input from block 72. The bit value for a given bin is one if the bin is occupied and zero if the bin is unoccupied.

At block 80 a BOC is computed upon expiration of a timer 74. The BOC is computed by summing the bit values of the bin occupancy bit vector stored at block 78. The BOC 58 is provided as output for use by atrial arrhythmia detection logic 60 (shown in FIG. 3). Upon providing the BOC 58 at the expiration of the timer 74, the bin occupancy bit vector is cleared by a reset signal 82 and timer 74 is reset. As such, timer 74 controls a time interval over which a $\delta RRI$ data stream is acquired and used for computing one BOC.

$\delta RRI$ bins may be defined according to a variety of schemes, with bins having equally spaced edges or unequally spaced edges. In one embodiment, bins are defined according to the following ranges: {[−2000, −504), [−504, −496), [−496, −488), . . . [−16, 16), [16, 24), . . . , [488, 496), [496, 504), [504, 2000)}. It is recognized that the BOC filter can be expanded to assign $\delta RRI$s to two-dimensional or higher-dimensional bins using the current $\delta RRI$ and previous $\delta RRI$s. For example, a two-dimensional (x, y) bin may be determined using the current $\delta RRI$ (x) and previous $\delta RRI$ (y).

Figure 5:
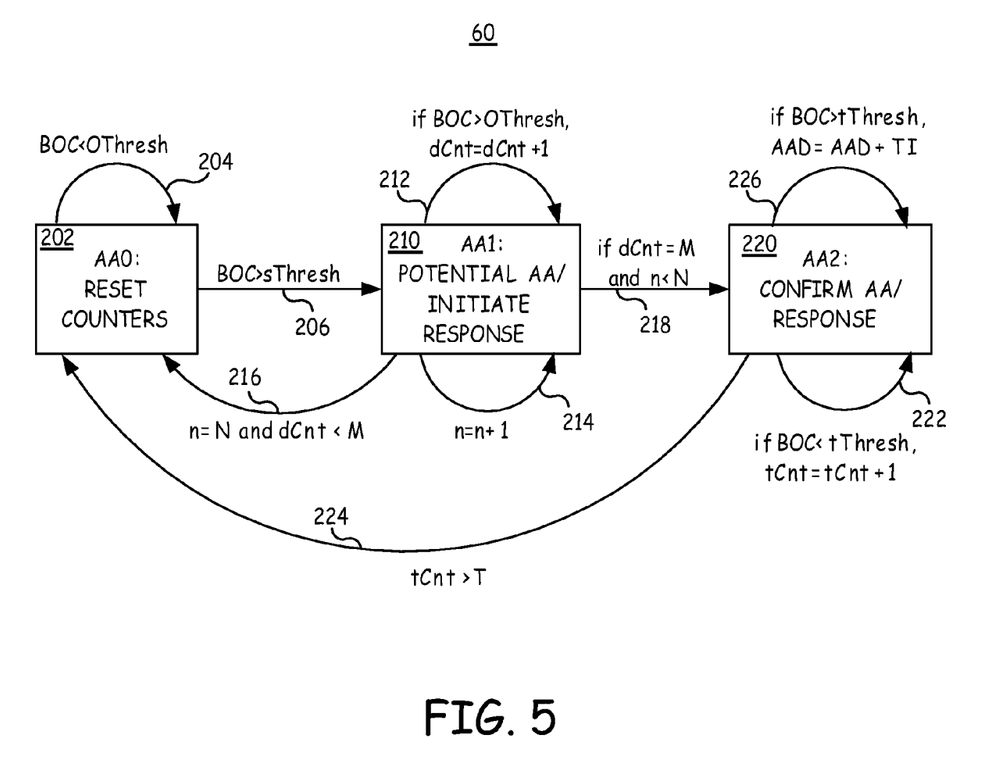
FIG. 5 is a state diagram of a method performed by an atrial arrhythmia detection logic block shown in FIG. 3 for identifying an atrial arrhythmia episode.

FIG. 5 is a state diagram of a method performed by AA detection logic block 60 of FIG. 3 for identifying an atrial arrhythmia episode. A logical state AA0 202 exists as long as the BOC value received from the BOC filter remains less than an atrial arrhythmia onset threshold (OThresh) as indicated by condition 204. If the BOC exceeds an onset threshold, a transition from AA0 state 202 to a potential atrial arrhythmia AA1 state 210 occurs as indicated by condition 206. AA1 state 210 may include initiating an atrial arrhythmia response. An atrial arrhythmia response may include preparing for or initiating an atrial therapy and/or storing diagnostic data. As will be described in greater detail below, diagnostic data may be stored upon transition from AA0 state 202 to AA1 state 210 for a predefined interval of time preceding the transition from AA0 state 202 to AA1 state 210.

In AA1 state 210, a detection counter (dCnt) is increased by one for each BOC that is above the onset threshold, as indicated by condition 212. For each BOC received while AA1 state 210 persists, i.e. for each timer interval that expires during the AA1 state 210, an interval counter n is increased by one as indicated by condition 214. If the interval counter n reaches a predetermined number N and the detection counter (dCnt) is less than a detection threshold number M defined for detecting an atrial arrhythmia, a transition back to AA0 state 202 occurs, as indicated by condition 216. The counters are reset to zero and the logic block 60 remains in AA0 state 202 until another BOC exceeds the onset threshold (condition 206).

If the detection counter reaches the detection threshold number (M) of BOCs exceeding the onset threshold before the interval counter (n) reaches the predetermined number of intervals (N), a state transition to AA2 state 220 occurs as indicated by condition 218. In other words, if at least M out of N BOCs exceed the onset threshold, the atrial arrhythmia detection is confirmed in AA2 state 220.

Any atrial arrhythmia response prepared for or initiated in AA1 state 210 may be continued or fully executed in AA2 state 220. Alternatively, a response may be initiated in AA2 state 220 after confirming the atrial arrhythmia episode.

In AA2 state 220, AA detection logic 60 monitors for the termination of the detected AA and computes a length of the AA episode. To monitor for termination of the AA episode, each BOC is compared to a termination threshold (tThresh). For each BOC that exceeds the termination threshold, an atrial arrhythmia duration (AAD) is computed by adding the timer interval used to compute the BOC to the current AAD value as indicated by condition 226. The AAD may be set to an initial value in AA1 state 210 corresponding to the threshold number M of BOCs which resulted in a state transition from AA1 state 210 to AA2 state 220.

For each BOC falling below the termination threshold causes a termination counter (tCnt) to be increased by one count as indicated by condition 222. The AA2 state 220 persists until a termination detection threshold number (T) of BOCs received from the BOC filter fall below a termination threshold (tThresh). If the termination counter exceeds the termination detection threshold number T defined for detecting the termination of the atrial arrhythmia episode, a state transition occurs back to AA0 state 202 as indicated by condition 224.

If a BOC is less than the termination threshold, but the termination counter (tCnt) has not yet reached the termination detection threshold number (T), termination is not detected. The timer interval for the BOC falling below tThresh may also be added to the atrial arrhythmia duration as long as termination is not yet detected. In alternative embodiments, the atrial arrhythmia duration is determined as the time between the state transition from AA0 state 202 to AA1 state 210 and the state transition from AA2 state 202 back to AA0 state 202. Alternatively, the atrial arrhythmia duration is determined as the time between the state transition from the AA1 state 210 to the AA2 state 220 and the state transition from the AA2 state 220 back to the AA0 state 202.

Figure 6:
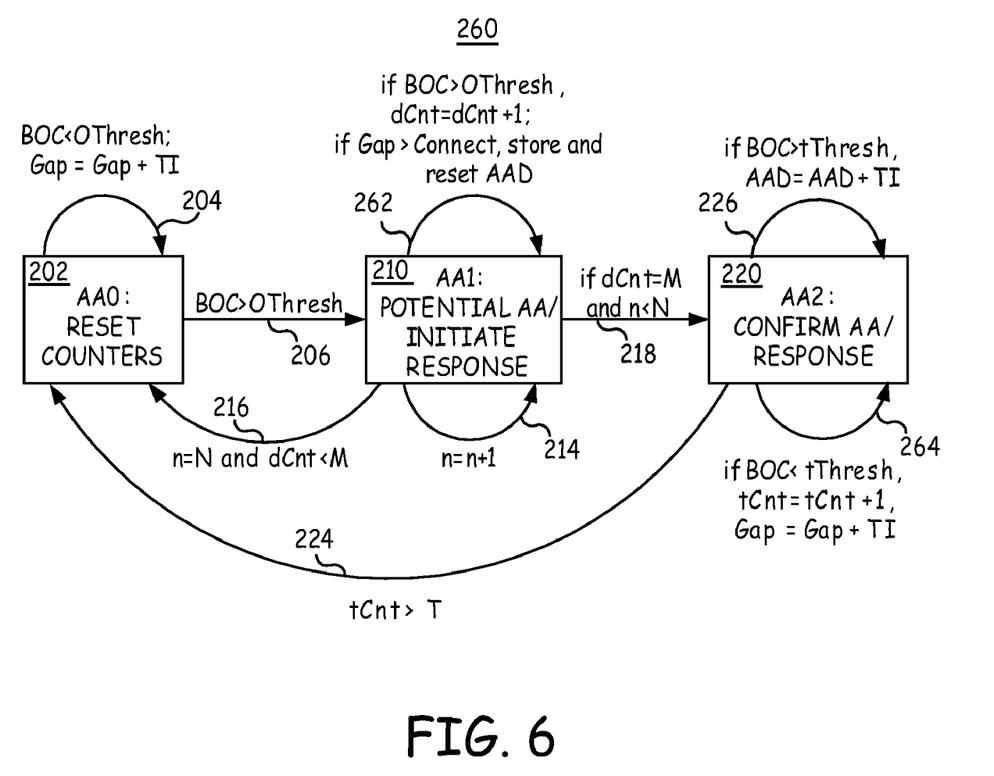
FIG. 6 is a state diagram of an alternative method for detecting an atrial arrhythmia.

FIG. 6 is a state diagram of an alternative method for detecting an atrial arrhythmia. Reference numerals shown in FIG. 6 correspond to identically numbered states or conditions shown in FIG. 5. In method 260, however a gap time between atrial arrhythmia detections is measured as indicated by condition 264. For each consecutive BOC falling below the termination threshold, a gap time is computed as the current value of the gap time plus one timer interval. After termination detection, a state transition occurs back to AA0 state 202 (condition 224). When another transition to AA1 state 210 occurs, i.e. a redetection of atrial arrhythmia evidence based on a BOC greater than the onset threshold (condition 206), the gap time is compared to a predetermined connect time at condition 262. If the gap time is greater than the connect time, the new potential atrial arrhythmia detection is considered a new arrhythmia episode. The current atrial arrhythmia duration (AAD) value is stored as the duration of the previously detected episode and then reset to determine the duration of the new episode as described previously. If the gap time is less than the connect time, the potential atrial arrhythmia and the previously detected atrial arrhythmia are considered one long episode. The atrial arrhythmia duration is not reset. When the new potential atrial arrhythmia is confirmed (condition 218), the atrial arrhythmia duration computed at condition 226 begins by adding appropriate time intervals to the previously determined atrial arrhythmia duration.

As long as gaps between consecutive atrial arrhythmia detections are less than the predetermined connect time, the detections are considered to be detections of one continuous atrial arrhythmia episode. A new response may or may not be provided at AA1 state 210 or AA2 state 220 when the gap time is less than the connect time. If a second detection occurs after a gap time greater than the programmed connect time, the episode is considered a new episode, and a new response is initiated at AA1 state 210 and/or AA2 state 220.

Figure 7:
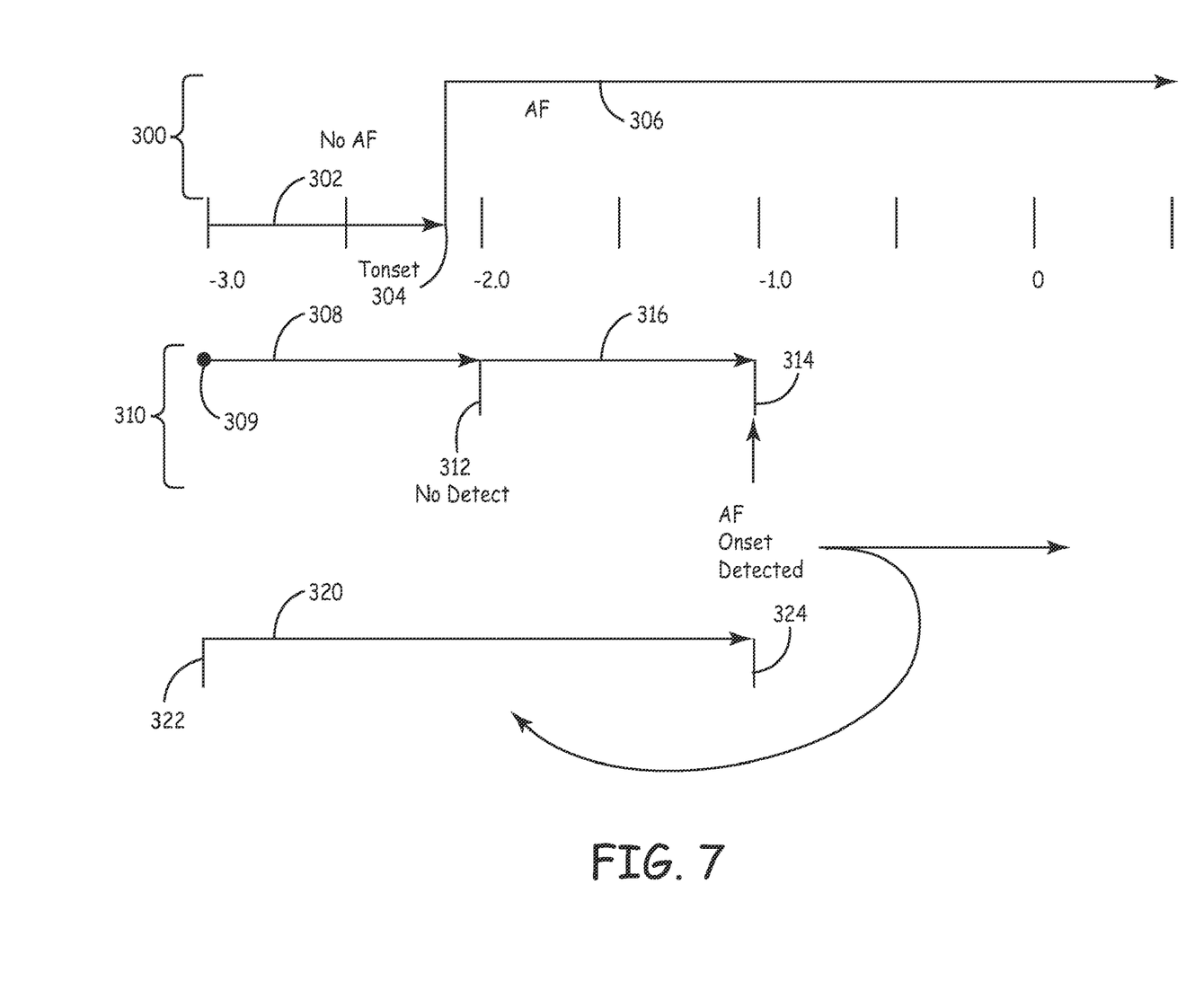
FIG. 7 is a timing diagram of an atrial arrhythmia detection and corresponding diagnostic data storage response.

FIG. 7 is a timing diagram of an atrial arrhythmia detection method and corresponding diagnostic data storage response. The data storage response to an atrial arrhythmia detection is provided for capturing the onset of an atrial arrhythmia. By the time detection criteria of an atrial arrhythmia detection algorithm are satisfied, the arrhythmia will be in progress with the actual onset occurring at a time earlier than the detection. The onset of an atrial arrhythmia episode may be of interest to a clinician since precipitating events can provide useful diagnostic information. Accordingly, various embodiments of the invention include methods for capturing and storing the onset of a detected atrial arrhythmia episode.

Timeline 300 depicts a period of no atrial arrhythmia 302, followed by the physiological onset 304 of an atrial arrhythmia episode 306. Timeline 310 corresponds to a series of time intervals 308 and 316. At the end of each time interval 308 and 316 a BOC is determined for detecting an atrial arrhythmia. Time interval 308 is shown to have a start time at 309 and an end time at 312. At the end 312 of the first time interval 308, the BOC criteria for detecting an atrial arrhythmia have not been met (i.e. the BOC is less than an onset threshold). Even though the atrial arrhythmia onset 304 occurred during the first time interval 308, the atrial arrhythmia was not detected. At the end 314 of the second time interval 316, an atrial arrhythmia detection is made based on the logic detection algorithm using BOCs as described previously. Upon detection of the atrial arrhythmia at 314, diagnostic data storage is triggered for storing the EGM/ECG signal for a predetermined data storage interval 320. Data storage window 320 has an end time 324 corresponding to the end 314 of time interval 316. The data storage interval 320 is shown to encompass at least one timer interval 308 preceding the timer interval 316 which resulted in the atrial arrhythmia detection at 314. Under some circumstances, for example when an atrial arrhythmia begins near the end of a timer interval, an atrial arrhythmia detection will not be made at the end of the time interval in which the atrial arrhythmia actually began. By providing a diagnostic data storage window encompassing both the timer interval 316 immediately preceding the arrhythmia detection and the preceding time interval 308, the physiological onset 304 of the atrial arrhythmia is recorded. The duration of the diagnostic data storage window may be twice the time interval used to determine a BOC. In one embodiment, each time interval 308 and 316 is about one minute and the data storage window triggered by an atrial arrhythmia detection is about two minutes.

Figure 8:
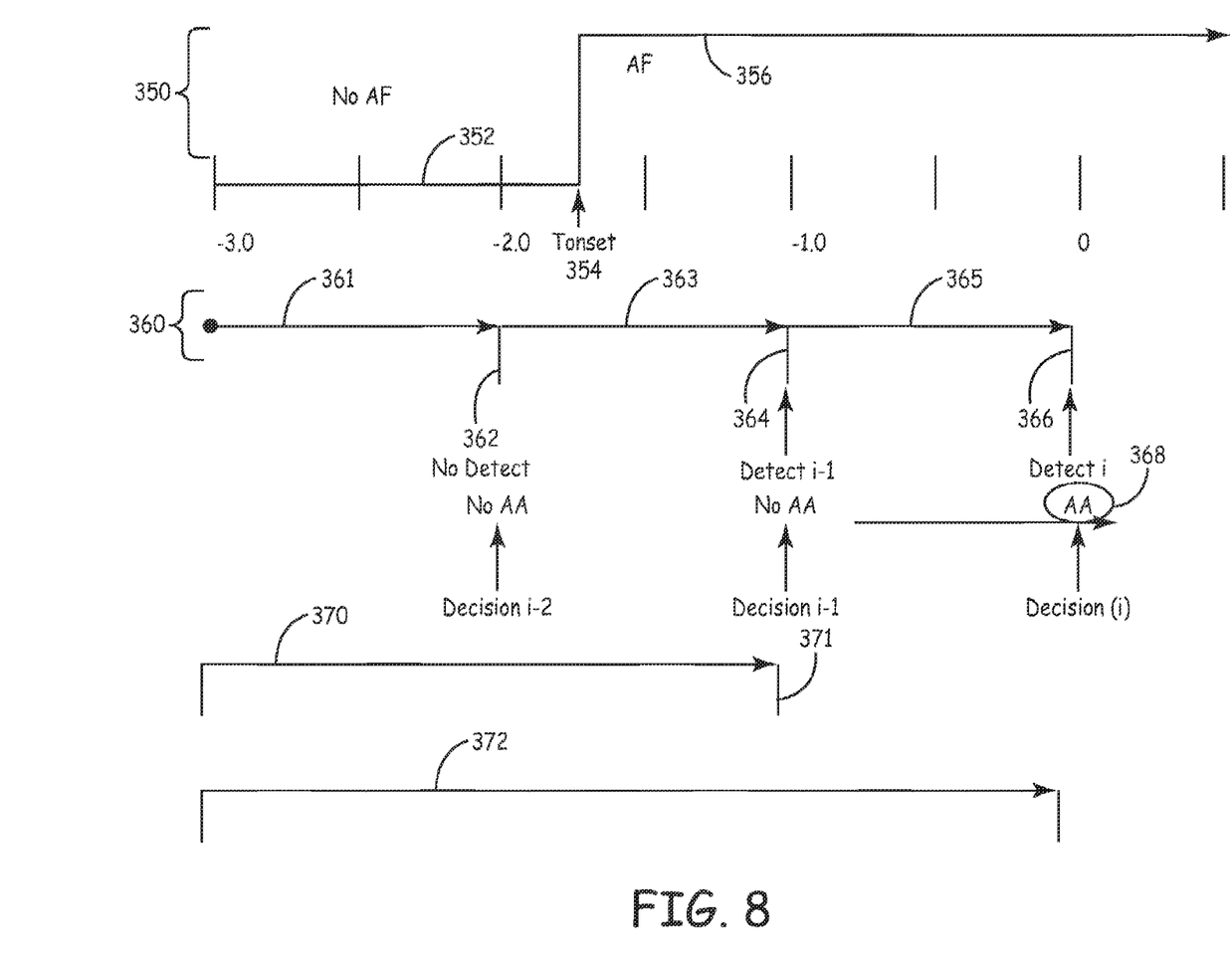
FIG. 8 is a timing diagram of an alternative embodiment for detecting an atrial arrhythmia and storing diagnostic data.

FIG. 8 is a timing diagram of an alternative embodiment for detecting an atrial arrhythmia and storing diagnostic data for capturing the onset of a detected atrial arrhythmia. Timeline 350 depicts a period of no atrial arrhythmia 352, followed by the physiological onset 354 of an atrial arrhythmia episode 356. Timeline 360 corresponds to a series of time intervals 361, 363, and 365. At the end of each time interval 361, 363 and 365 a BOC is determined as described previously for detecting an atrial arrhythmia. In the method illustrated in FIG. 8, the results at the end of two consecutive timer intervals are used for making a decision whether atrial arrhythmia is present. At the end of the first time interval 361, the BOC detection threshold has not been met resulting in a no detect signal at 362. The onset 354 of the atrial arrhythmia occurs during the second timer interval 363. At the end of the second timer interval 363, the atrial arrhythmia BOC detection threshold is met resulting in a detect signal at 364 as evidence of an atrial arrhythmia being present. A pooled decision criterion is applied that requires two consecutive detect signals to occur in order to confirm an atrial arrhythmia. The decision made at 364 considers the atrial arrhythmia evidence determined during the first time interval 361 and the second time interval 363 for detecting the atrial arrhythmia. The detect signal at 364 and the no detect signal at 362 results in no atrial arrhythmia detection at 364. At the end 366 of the next timer interval 365, the BOC detection threshold is met again resulting in a detect signal at 366 as evidence of an atrial arrhythmia. The decision made at 366 considers the detect signal at 354 and the detect signal at 366 resulting in a confirmed atrial arrhythmia detection at 366. The detection of the atrial arrhythmia at 366 is based on pooling the arrhythmia evidence of the previous two time intervals 363 and 365. Upon detection at 366, a diagnostic data storage window 370 is triggered for storing the EGM/ECG signal. The end time 371 of the data storage window 370 ends at the end 364 of time interval 363, when the first detect signal was generated. The data storage window 370 is shown to encompass at least a portion of one timer interval 361 preceding the timer interval 363 which resulted in the first detect signal at 364. The diagnostic data storage window 370 may be twice the timer interval used to determine a BOC. An alternative diagnostic data storage interval 372 may end concomitantly with the atrial arrhythmia detection at 366 based on pooled atrial arrhythmia evidence determined at the end of each time interval 361, 363, and 365 and may encompass all three preceding time intervals 361, 363 and 365. While each time interval 361, 363 and 365 is shown to be one minute in length with atrial arrhythmia evidence from two consecutive time intervals pooled for making an atrial arrhythmia detection decision, it is recognized that other time interval lengths and number of time intervals may be used for making atrial arrhythmia detections.

Figure 9:
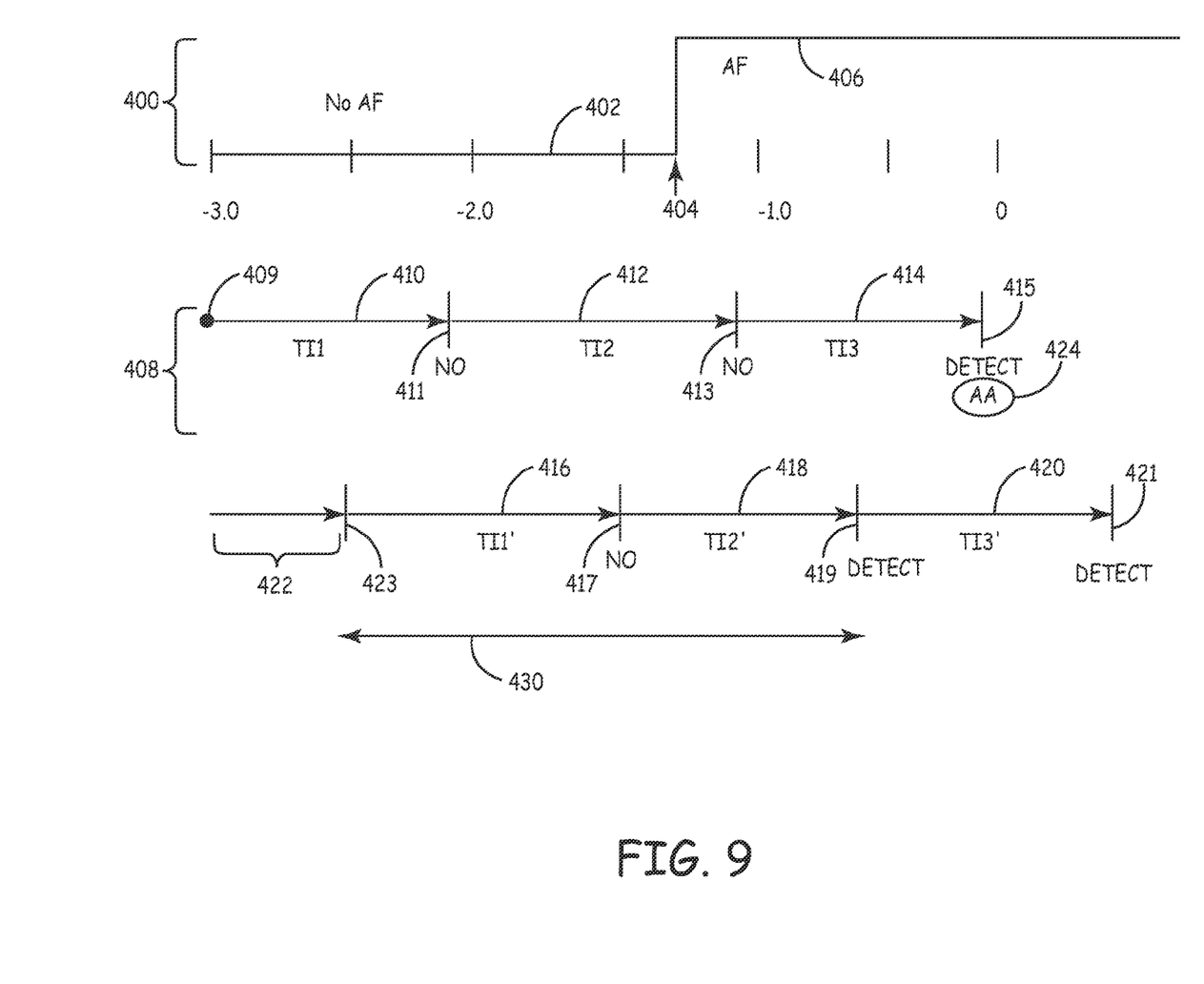
FIG. 9 is a timing diagram of yet another method for detecting an atrial arrhythmia and storing diagnostic data.

FIG. 9 is a timing diagram of yet another method for detecting an atrial arrhythmia and storing diagnostic data. In the method shown in FIG. 9, staggered timer intervals are used for determining BOCs at more frequent intervals while still allowing the BOCs to be determined without shortening the time interval over which a BOC is determined. Timeline 400 depicts a period of no atrial arrhythmia 402 followed by the physiological onset 404 of an atrial arrhythmia episode 406. Timelines 408 represent staggered time intervals that are applied simultaneously for determining BOCs at more frequent intervals. Time intervals 410, 412 and 414 may each be one minute (or another duration) in length. At the end of each time interval 410, 412, and 414 a "no detect" or a "detect" signal is generated based on the atrial arrhythmia evidence determined as a BOC exceeding an onset threshold. Timer intervals 416, 418, and 420 are equal in length to timer intervals 410, 412, and 414. The start time of each of time intervals 416, 418 and 420 is staggered relative to the start time of intervals 410, 412, and 414. The lag 422 between the start time 409 of time interval 410 and the start time 423 of time interval 416 may be approximately one-half the duration of time intervals 410 and 416, though shorter or longer lag times may be used. In some embodiments, the leading time intervals 410, 412, and 414 may have a different duration than the lagging time intervals 416, 418, and 420.

At the end 411 of time interval 410, a "no detect" signal is generated based on the BOC. Likewise, a "no detect" signal is generated at the end 417 of time interval 416. The physiological onset 404 of the atrial arrhythmia occurs during time interval 412 and time interval 418. A "no detect" signal is generated at the end 413 of time interval 412 because the arrhythmia onset 404 occurs near the end of time interval 412, resulting in the BOC being less than the onset threshold for interval 412. A "detect" signal is generated at the end 419 of time interval 418 and at the end of the subsequent time intervals 414 and 420, at 415 and 421, respectively, during the atrial arrhythmia episode 406. In one embodiment, an atrial arrhythmia detection is made upon the first detect signal at 419 at the end of timer interval 418, triggering a diagnostic data storage window 430. The data storage window 430 includes at least a portion of the preceding timer intervals 412 and 416.

In an alternative embodiment, an atrial arrhythmia detection is made using pooled data from any number of the consecutive, staggered timer intervals 410, 412, 414, 416, 418 and 420. An atrial arrhythmia detection 424 may be made at the end 415 of timer interval 414 based on the two consecutive "detect" signals at 415 and 419. The atrial arrhythmia detection 424 triggers a diagnostic data storage window 430 which ends concomitantly with the first detect signal at 419 and includes at least a portion of the previous timer intervals 412 and 416. Alternatively, data storage window 430 may end concomitantly with the atrial arrhythmia detection 424 at the end of timer interval 414 and include at least a portion of the preceding timer interval 412. It is recognized that numerous timing schemes may be conceived for positioning a diagnostic data storage window previous to the atrial arrhythmia detection 424 such that the physiological onset 404 of an atrial arrhythmia episode 406 is captured and recorded for diagnostic purposes.

Figure 10:
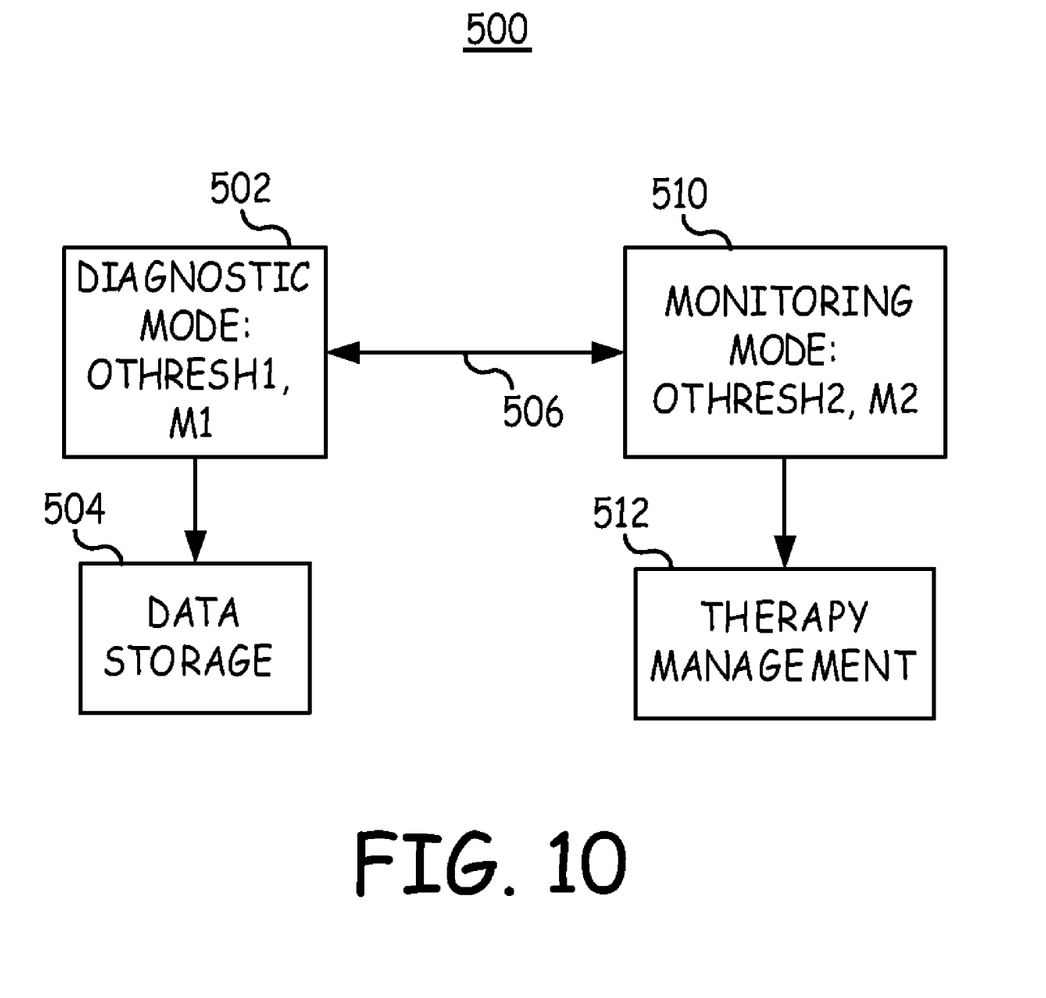
FIG. 10 is a flow chart of a method of operation for a medical device configured to detect atrial arrhythmias using RR interval irregularity.

FIG. 10 is a flow chart of a method of operation for a medical device configured to detect atrial arrhythmias using RR interval irregularity. Method 500 includes two medical device operating modes 502 and 510 which may be selectively programmed 506 by a clinician. In the diagnostic mode 502, atrial arrhythmia detection methods are used for triggering data storage 504 for diagnostic purposes. An onset threshold (OThreash1) and a detection threshold number (M1) used by BOC detection logic may be set relatively low to provide a high sensitivity to atrial arrhythmias. Data storage 504 is enabled to allow EGM/ECG data to be recorded to capture the onset of a detected atrial arrhythmia. The low threshold settings may result in some false detections which can be verified using the recorded data.

In monitoring mode 510, a different onset threshold (OThresh2) and detection threshold number (M2) may be used by the detection logic for detecting atrial arrhythmias. The onset threshold and the detection threshold number may be optimized based on performance of the device operating in the diagnostic mode and may be set higher than during the diagnostic mode to provide greater accuracy of atrial arrhythmia detections. The data storage 504 is optional during the monitoring mode. Atrial arrhythmia detections made during the monitoring mode 510 may be used primarily as feedback for therapy management 512. Therapy management may include controlling the delivery of electrical stimulation therapies, drug therapies, or the like.

Thus, methods and apparatus for detecting atrial arrhythmias have been presented in the foregoing description with reference to specific embodiments. It is appreciated that various modifications to the referenced embodiments may be made without departing from the scope of the invention as set forth in the following claims.

The invention claimed is:

1. A method for detecting atrial arrhythmias, comprising:
   acquiring a cardiac signal, the cardiac signal including R-waves;
   computing a plurality of RR interval differences between pairs of consecutive RR intervals of the cardiac signal occurring during a first time interval, the first time interval having a start time and an end time;
   detecting an atrial arrhythmia subsequent to the end time of the first time interval in response to the computed differences; and
   triggering storage of the cardiac signal for a second time interval in response to the atrial arrhythmia detection, the second time interval having a start time prior to the atrial arrhythmia detection.

2. The method of claim 1 wherein the second time interval corresponds to an onset time of the detected atrial arrhythmia.

3. The method of claim 1 wherein the second time interval includes a start time occurring prior to the start time of the first time interval.

4. The method of claim 1 wherein the second time interval includes an end time occurring concomitant with the start time of the first time interval.

5. The method of claim 1 wherein detecting an atrial arrhythmia subsequent to the end of the first time interval comprises:
   computing a plurality of RR interval differences between pairs of consecutive RR intervals for a previous time interval having an end time preceding the end time of the first time interval;
   determining atrial arrhythmia evidence during the previous time interval in response to the computed differences;
   determining atrial arrhythmia evidence during the first time interval in response to the computed differences; and
   detecting the atrial arrhythmia at the end of the first time interval in response to the atrial arrhythmia evidence determined during the previous time interval and the atrial arrhythmia evidence determined during the first time interval.

6. The method of claim 5 wherein the atrial arrhythmia is not detected at the end of the preceding time interval and the second time interval comprises the first time interval and the preceding time interval.

7. The method of claim 1 further comprising setting RR interval acceptance criteria, wherein computing the plurality of RR interval differences comprises rejecting RR intervals not meeting the RR interval acceptance criteria.

8. The method of claim 1 further comprising:
configuring a plurality of RR interval difference bins corresponding to R-R interval difference ranges;
assigning a computed RR interval difference to an RR interval difference bin corresponding to the computed RR interval difference; and
determining an occupied bin count at the first time interval end time, wherein detecting the atrial arrhythmia comprises comparing the occupied bin count to an onset threshold.

9. The method of claim 8 wherein detecting the atrial arrhythmia further comprises:
setting a detection threshold number;
determining an occupied bin count at the end of a plurality of time intervals preceding the first time interval; and
determining a number of the occupied bin counts exceeding the onset threshold, wherein detecting the atrial arrhythmia subsequent to the end time of the first time interval occurs in response to the determined number of the occupied bin counts exceeding the onset threshold exceeding the detection threshold number.

10. The method of claim 8 further comprising selecting one of a diagnostic mode and a monitoring mode wherein the onset threshold being set to a first value during the diagnostic mode and to a second value during the monitoring mode, wherein the second value being greater than the first value.

11. The method of claim 8 further comprising selecting one of a diagnostic mode and a monitoring mode wherein the triggered storage of the cardiac signal is suspended during the monitoring mode.

12. The method of claim 1 further comprising:
computing a plurality of differences between pairs of consecutive RR intervals occurring during a plurality of time intervals subsequent to the first time interval; and
detecting an atrial arrhythmia termination in response to the computed differences between pairs of consecutive RR intervals occurring during the plurality of time intervals subsequent to the first time interval
the second time interval having an end time subsequent to the end time of the first time interval.

13. The method of claim 12 wherein detecting the atrial arrhythmia termination comprises:
configuring a plurality of RR interval difference bins corresponding to RR interval difference ranges;
assigning a computed RR interval difference to an RR interval difference bin corresponding to the computed RR interval difference;
setting a termination threshold and a termination detection threshold number;
determining an occupied bin count at the end of each of the plurality of time intervals subsequent to the first time interval;
determining a number of the occupied bin counts being less than the termination threshold; and
detecting a termination of the atrial arrhythmia in response to the number of occupied bin counts being less than the termination threshold exceeding the termination detection threshold number.

14. The method of claim 12 further comprising:
defining a connect time;
detecting a next atrial arrhythmia;
computing a gap time between the detected termination of the atrial arrhythmia and the detected next atrial arrhythmia, and
detecting a continuous atrial arrhythmia episode in response to the gap time being less than the connect time.

15. A computer-readable medium for storing a set of instructions which when implemented in a system cause the system to:
acquire a cardiac signal, the cardiac signal including R-waves;
compute a plurality of RR interval differences between pairs of consecutive RR intervals occurring during a first time interval, the first time interval having a start time and an end time;
detect an atrial arrhythmia subsequent to the end time of the first time interval in response to the computed differences; and
trigger storage of the cardiac signal for a second time interval in response to the atrial arrhythmia detection, wherein the second time interval having a start time prior to the atrial arrhythmia detection and an end time subsequent to the end time of the first time interval.

16. A medical device system, comprising:
an electrode for acquiring a cardiac signal, the cardiac signal including R-waves;
a memory to store the cardiac signal; and
a control module, coupled to the electrode, to compute a plurality of RR interval differences between pairs of consecutive RR intervals occurring during a first time interval, the first time interval having a start time and an end time, detect an atrial arrhythmia subsequent to the end time of the first time interval in response to the computed differences, and trigger storage of the cardiac signal in the memory for a second time interval in response to the atrial arrhythmia detection, the second time interval having a start time prior to the atrial arrhythmia detection.

17. The system of claim 16 wherein the second time interval includes an onset time of the detected atrial arrhythmia.

18. The system of claim 16 wherein the second time interval is greater than the first interval of time.

19. The system of claim 16 wherein the second time interval includes a start time occurring prior to the start time of the first time interval.

20. The system of claim 16 wherein the second time interval includes an end time, the end time occurring concomitant with the start time of the first time interval.

21. The system of claim 16 wherein the control module computes a plurality of RR interval differences between pairs of consecutive RR intervals for a previous time interval having an end time preceding the first time interval end time; determines atrial arrhythmia evidence during the previous time interval in response to the computed differences, determines atrial arrhythmia evidence during the first time interval in response to the computed differences, and detects the atrial arrhythmia at the end of the first time interval in response to the atrial arrhythmia evidence determined during the previous time interval and the atrial arrhythmia evidence determined during the first time interval.

22. The system of claim 16 wherein the control module sets RR interval acceptance criteria and rejects RR intervals not meeting the RR interval acceptance criteria.

23. The system of claim 16 wherein the control module generates a plurality of RR interval difference bins corresponding to R-R interval difference ranges, assigns a computed RR interval difference to an RR interval difference bin corresponding to the computed RR interval differences, and determines an occupied bin count at the first time interval end time, and compares the occupied bin count to an onset threshold to detect the atrial arrhythmias.

24. The system of claim 23 wherein the control module sets a detection threshold number, determines an occupied bin count at the end of a plurality of time intervals preceding the first time interval, determines a number of the occupied bin counts exceeding the onset threshold, and detects the atrial arrhythmia subsequent to the end time of the first time interval in response to the number of the occupied bin counts exceeding the onset threshold exceeding the detection threshold number.

25. The system of claim 23 wherein the control module selects one of a diagnostic mode and a monitioring mode, and wherein the onset threshold is set to a first value during the diagnostic mode and to a second value, greater than the first value, during the monitoring mode.

26. The system of claim 16 wherein the control module determines a plurality of differences between pairs of consecutive RR intervals occurring during a plurality of time intervals subsequent to the first time interval, and detects an atrial arrhythmia termination in response to the determined differences between pairs of consecutive RR intervals occurring during the plurality of time intervals subsequent to the first time interval, the second time interval having an end time subsequent to the end time of the first time interval.

27. The system of claim 26 wherein the control module determines RR interval difference bins corresponding to RR interval difference ranges, assigns an RR interval difference to an RR interval difference bin corresponding to the computed RR interval difference, sets a termination threshold and a termination detection threshold number, determines an occupied bin count at the end of each of the plurality of time intervals subsequent to the first time interval, determines a number of the occupied bin counts being less than the termination threshold, and detects a termination of the atrial arrhythmia in response to the number of occupied bin counts being less than the termination threshold exceeding the termination detection threshold number.

28. The system of claim 26 wherein the control module determines a connect time, computes a gap time between the detected termination of the atrial arrhythmia and the detected next atrial arrhythmia, and detects a continuous atrial arrhythmia episode in response to the gap time being less than the connect time.

* * * * *

UNITED STATES PATENT AND TRADEMARK OFFICE
CERTIFICATE OF CORRECTION

PATENT NO. : 7,634,310 B2  Page 1 of 1
APPLICATION NO. : 11/554275
DATED : December 15, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 84 days.

Signed and Sealed this

Ninth Day of November, 2010

David J. Kappos
*Director of the United States Patent and Trademark Office*